(12) United States Patent
Babichenko et al.

(10) Patent No.: US 10,041,882 B2
(45) Date of Patent: Aug. 7, 2018

(54) DEVICE FOR REMOTE OIL DETECTION

(71) Applicant: LDI INNOVATION OÜ, Tallinn (EE)

(72) Inventors: Sergey Babichenko, Tallinn (EE); Leino Vint, Tallinn (EE)

(73) Assignee: Ocean Visuals AS, Alesund (NO)

( * ) Notice: Subject to any disclaimer, the term of this patent is extended or adjusted under 35 U.S.C. 154(b) by 32 days.

(21) Appl. No.: 15/027,462

(22) PCT Filed: Nov. 21, 2014

(86) PCT No.: PCT/EE2014/000008
§ 371 (c)(1),
(2) Date: Apr. 6, 2016

(87) PCT Pub. No.: WO2015/074669
PCT Pub. Date: May 28, 2015

(65) Prior Publication Data
US 2016/0252457 A1   Sep. 1, 2016

(30) Foreign Application Priority Data

Nov. 25, 2013 (EE) ................. 201300092 U

(51) Int. Cl.
*G01N 21/64* (2006.01)
*G01S 17/88* (2006.01)
(Continued)

(52) U.S. Cl.
CPC ......... *G01N 21/6402* (2013.01); *G01N 21/15* (2013.01); *G01N 21/643* (2013.01);
(Continued)

(58) Field of Classification Search
None
See application file for complete search history.

(56) References Cited

U.S. PATENT DOCUMENTS 3,899,213 A * 8/1975 Fantasia ................. G01N 21/64
250/301
5,461,473 A * 10/1995 Pratt ................... G01C 15/002
250/206.1
(Continued)

FOREIGN PATENT DOCUMENTS

EP      0 074 441 A1   3/1983
JP     2012-005991 A   1/2012
(Continued)

OTHER PUBLICATIONS

S. Babichenko, etal.: Airborne surveillance of water basins with hyperspectral FLS-LiDAR; vol. 7825; Oct. 6, 2010; p. 78250K; XP055167258; ISSN: 0277-786X; DOI: 10.1117/12.864944; p. 2; Paragraph 2.1; Figure 1.
(Continued)

*Primary Examiner* — Edwin Gunberg
(74) *Attorney, Agent, or Firm* — Ladas & Parry LLP

(57) ABSTRACT

This relates to the field of real-time detection of chemical contamination of water in harsh environmental conditions by using laser remote sensing apparatus for detection of oil or oil products. In-time detection and localization of oil pollution in seawater are the measures to minimize potential damages to the marine and coastal environment. A technical solution for remote detection and classification of chemical pollution in water, to optimize operational parameters, weight, size and power consumption of such device, to make possible continuous unattended operation of such device on board of a moving or stationary platform and to provide data processing and reporting the results through communication channels is described.

17 Claims, 5 Drawing Sheets

(51) Int. Cl.
*G01N 21/15* (2006.01)
*G01N 33/18* (2006.01)

(52) U.S. Cl.
CPC ..... *G01N 21/6456* (2013.01); *G01N 33/1833* (2013.01); *G01S 17/88* (2013.01); *G01N 2201/0227* (2013.01)

(56) References Cited

U.S. PATENT DOCUMENTS

| | | | | |
|---|---|---|---|---|
| 8,599,649 | B1* | 12/2013 | Antonelli | G01H 9/00 367/149 |
| 2006/0152705 | A1 | 7/2006 | Yoshida et al. | |
| 2007/0221863 | A1* | 9/2007 | Zipf | G01N 21/631 250/461.1 |
| 2008/0141636 | A1 | 6/2008 | Singh | |
| 2010/0132804 | A1* | 6/2010 | Kereth | H05K 5/068 137/171 |
| 2010/0188659 | A1 | 7/2010 | Shver | |

FOREIGN PATENT DOCUMENTS

| | | |
|---|---|---|
| WO | 2007/012878 A1 | 2/2007 |
| WO | 2010/128860 A1 | 11/2010 |
| WO | 2012/006826 A1 | 1/2012 |
| WO | 2013/007982 A1 | 1/2013 |
| WO | 2013/087799 A1 | 6/2013 |

OTHER PUBLICATIONS

Sergey Babichenko, et al; Submerged-oil tracking by airborne hyperspectral fluorescent lidar; SPIE Newsroom: Dec. 21, 2010; XP055167054; DOI: 10.1117/2. 1201011, 003273.
English Abstract of WO 2012/006826 A1.
Sergey Babichenko: Laser Remote Sensing of the European Marine Environment: LIF Technology and Applications. In "Remote Sensing of the European Seas", Vittorio Barale and Martin Gade (Editors); Springer; 2008; 189-204.
I.Sobolev and Sergey Babichenko: Analysis of the performances of hyperspectral lidar for water pollution diagnostics; EARSEL e-Proceedings; vol. 12, No. 2; 2013, 113-123.
English Abstract of JP 2012-05991A.

* cited by examiner

DEVICE FOR REMOTE OIL DETECTION

RELATED APPLICATION

This application is a national phase entry under 35 USC 371 of international Patent Application No PCT/EE2014/000008 filed on 21 Nov. 2014, which claims priority from Estonian Application No. U201300092 filed on 25 Nov. 2013.

FIELD OF THE INVENTION

The invention relates to the field of real-time detection of chemical contamination of natural-, processed and run-off water in harsh environmental conditions by using laser remote sensing apparatus of original design.

BACKGROUND OF THE INVENTION

In-time detection, localization and optimal clean-up of oil pollution in seawater are all measures to minimize potential damage to the marine and coastal environment. Among other remote sensing techniques used for oil-in-water detection, the laser remote sensing systems (LIDAR) can be specified as advanced sensor for near-range detection, facilitating direct oil measurement and classification (S. Babichenko. Laser Remote Sensing of the European Marine Environment: LIF technology and Applications. In "Remote Sensing of the European Seas", Vittorio Barale and Martin Gade (Editors), Springer, 2008, 189-204), [1].

LIF LIDAR is based on the detection and analysis of the spectra of Laser Induced Fluorescence (LIF) of water due to its illumination with laser radiation. Hyperspectral LIF (HLIF) LIDAR is characterised with its ability to detect and classify oil pollution in water. When the laser pulse hits the water, it is absorbed by the molecules of water and other substances. The molecules re-emit absorbed energy in a certain spectral ranges, and the spectrum of such induced emission is characteristic for the type of molecule. This re-emitted signal is detected by the receiving system of HLIF LIDAR, and its spectral properties are analyzed to obtain information on a composition of compounds in water (I. Sobolev, S. Babichenko, Analysis of the performances of hyperspectral lidar for water pollution diagnostics. EARSEL e-Proceedings, Vol. 12, No. 2, 2013, 113-123), [2].

The HLIF LIDAR installed on board of the travelling ship is able to provide underway continuous detection of oil in water with high (few meters) spatial resolution. The HLIF LIDAR installed on stationary platform, including off-shore platforms, is able to continuously monitor the controlled water areas. High sensitivity and high sampling rate (e.g. 10 measurements per second) provide effective tool for early in time detection of oil leaks. The sensitivity of HLIF LIDAR allows oil detection in concentration range from 1 ppm (part per million) up to oil film stage. In such installations the HLIF LIDAR is able to detect oil film on the water surface, oil emulsion and submerged oil in water column, also both in iced water (S. Babichenko, D. Beynon, and K. O'Neill (2010), Submerged-oil tracking by airborne hyperspectral fluorescent lidar. SPIE Newsroom 10.1117/2.1201011.003273), [3].

Operational use of HLIF LIDAR should meet manifold of requirements. Firstly, for efficient use it should operate continuously and in unattended mode. Secondly, it should be applicable on the open decks of the ships or platforms with easy installation. Thirdly, it should handle harsh environmental conditions, namely high salinity, humidity and low temperature specifically for operation in the near-polar waters.

The technical means to eliminate the influence of marine mist to the onboard equipment have been intensively developed in the last decades. In particular the patent document EP0074441, 1983, "Improved method for removing moisture particles", [4] disclosed the improved method for removing moisture particles containing salt. The patent document US2008141636 "Moisture removal apparatus and method", [5] disclosed the apparatus and method for moisture removal in marine airflow. The Invention "Moisture removal filter", JP2012005991, 2012, [6] describes moisture removal filter capable to minimize the humidity in the airflow. The invention WO2013007982 [7] provides the technical solution for supplying a flow of dehumidified air to the interior of the cargo storage compartment.

SUMMARY OF INVENTION

An object of the present invention is to provide a technical solution for remote detection and classification of chemical pollution in water especially at harsh environmental conditions, namely at high humidity and salinity, and at low ambient temperature.

Another object is to optimize operational parameters, weight, size and power consumption of such device.

Next object is to make possible continuous unattended operation of such device on board of a moving or stationary platform to reliably locate oil seeps and spills on water surface and in water body.

Further object is to provide data processing and reporting the results through communication channels with limited availability.

It is realized with the laser remote sensing spectrometer (LIDAR) of original design (FIG. 1) comprising of: external housing 1 mounted on the platform with the ambient air intake 2 and outlet window 3 providing direct line of sight to the water surface; mist removal system 4 providing air flow drying and desalination; heater 5 with temperature sensor; internal housing 6 with modular LIDAR; laser emitter module 7 to sense the water and induce oil fluorescence; receiving module 8 including optical telescope and spectral detection block to detect the Laser Induced Fluorescence (LIF) spectrum of echo-signal; microcontroller module 9 to control LIDAR operation and form digitized data; internal outlet optical window 10; communication, data processing and storage module 11 for data analysis and reporting.

The device has modular structure.

DETAILED DESCRIPTION OF THE INVENTION

To provide device operation at harsh environmental conditions, namely high humidity and salinity, and low temperature, the following technical solutions are used.

Figure 1:
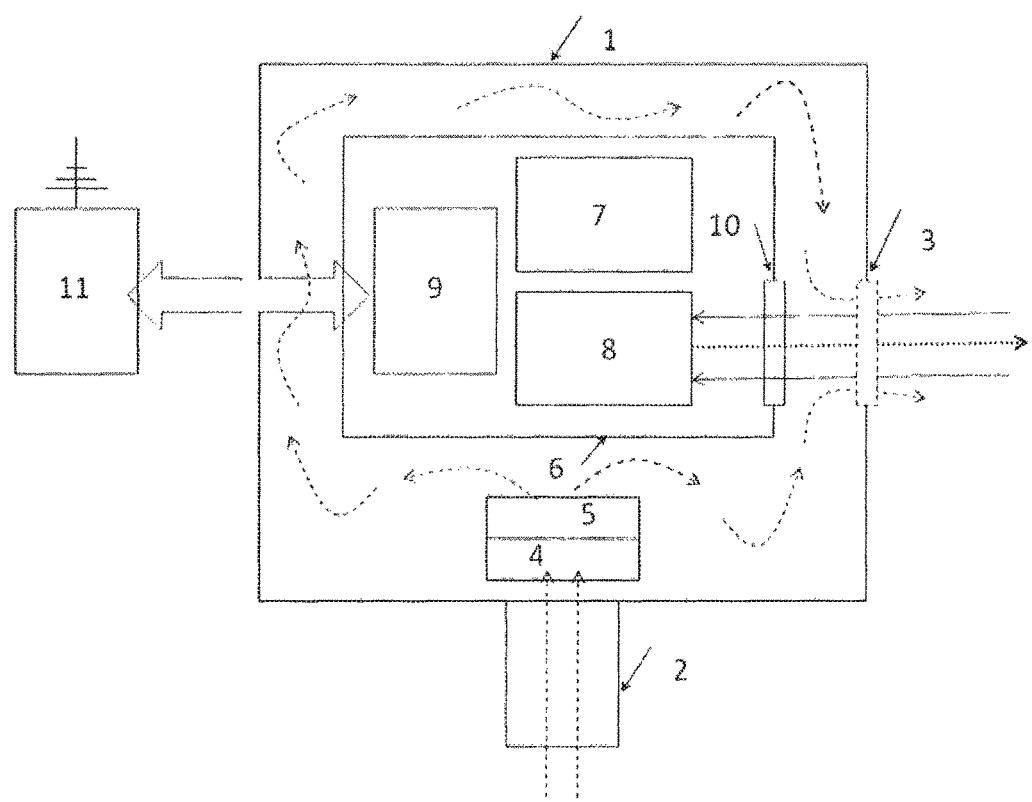
FIG. 1: Block-scheme of the Device for remote oil detection in harsh marine environment: 1—external housing; 2—ambient air intake; 3—outlet window with opening cap; 4—mist removal system; 5—heater with temperature sensor; 6—internal housing; 7—laser emitter module; 8—control and receiving module; 9—microcontroller module; 10—internal optical window; 11—storage and communication module.

In the first embodiment (FIG. 1) the LIDAR is designed inside the hermetical internal housing 6 filled with $N_2$ at overpressure. The internal housing is located inside the external one containing ambient air intake 2 and open outlet window 3 with closing cap. The inlet airflow is dried, desalinated and heated with the mist removal system 4. The air flow is arranged with air pump at higher than atmosphere pressure thus providing the air circulation through the external housing 1 with air exhaust through the open outlet window 3. In this way the optical window 9 is kept dry and clean. The laser beam and received fluorescence signal are directed through the internal optical window 10. The heater 5 controlled by temperature sensor keeps the LIDAR in internal housing 6 at the preset temperature for effective operation. To keep the device operational, the airflow should run continuously with no stops. Then the LIDAR can operate completely unattended. The outlet window 3 is closed with the cap for LIDAR storage and transportation.

The modern ships often have the system of technical airflow, already containing the mist removal, desalination and heating functions. If such airflow is available, the mist removal block 4 can be omitted, and the air intake 2 can be directly connected to such air flow.

Figure 2:
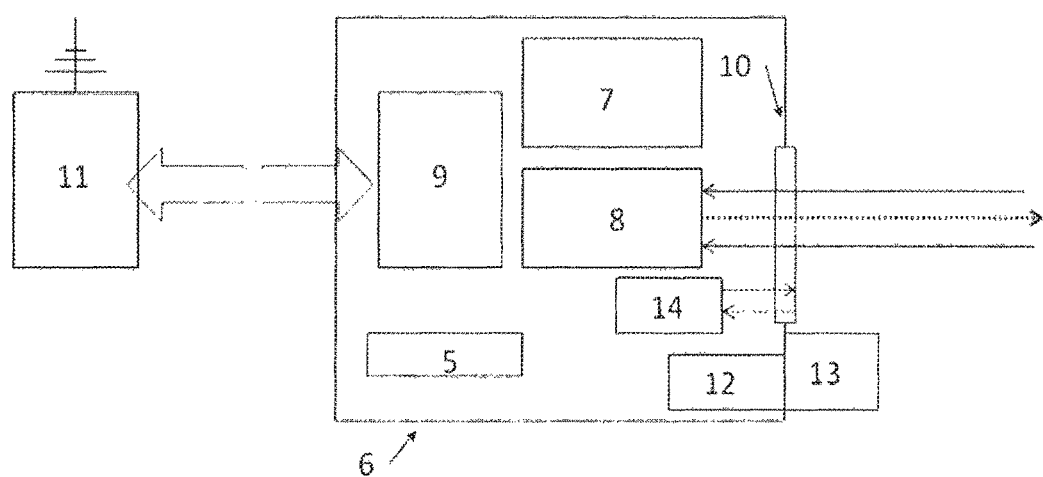
FIG. 2: Block scheme of the Device for remote oil detection without ambient air intake: 5—heater with temperature sensor; 6—hermetical housing; 7—laser emitter module; 8—control and receiving module; 9—LIDAR microcontroller module; 10—optical window; 11—storage and communication module; 12—flushing module for cleaning liquid; 13—cleaning liquid module; 14—optical sensor for window contamination detection.

In another embodiment (FIG. 2) the LIDAR is designed in a single hermetical housing 6 filled with $N_2$ at overpressure and containing heater with temperature sensor 5 inside such housing. Such design provides keeping the operational temperature of the LIDAR at the pre-set level, and protects the optical window 10 against frost. Such design will require periodical flush of cleaning liquid to eliminate possible salt residuals on the external surface of the optical window 10 or manual cleaning of the window. To do it the flush module 12 with external cleaning liquid volume 13 are used. The optical sensor 14 serves to detect the contamination of the external surface of the optical window 10.

The microcontroller module 9 is equipped with GPS receiver and has optional inputs for other sensors including but not limited to Inertial Measurement Unit (IMU) for better geo-positioning, temperature, wind, salinity etc. The module 9 serves to control operation of the LIDAR according to pre-set operational cycle and transmit the measured spectral and accompanying data to the storage and communication module 11.

Figure 3:
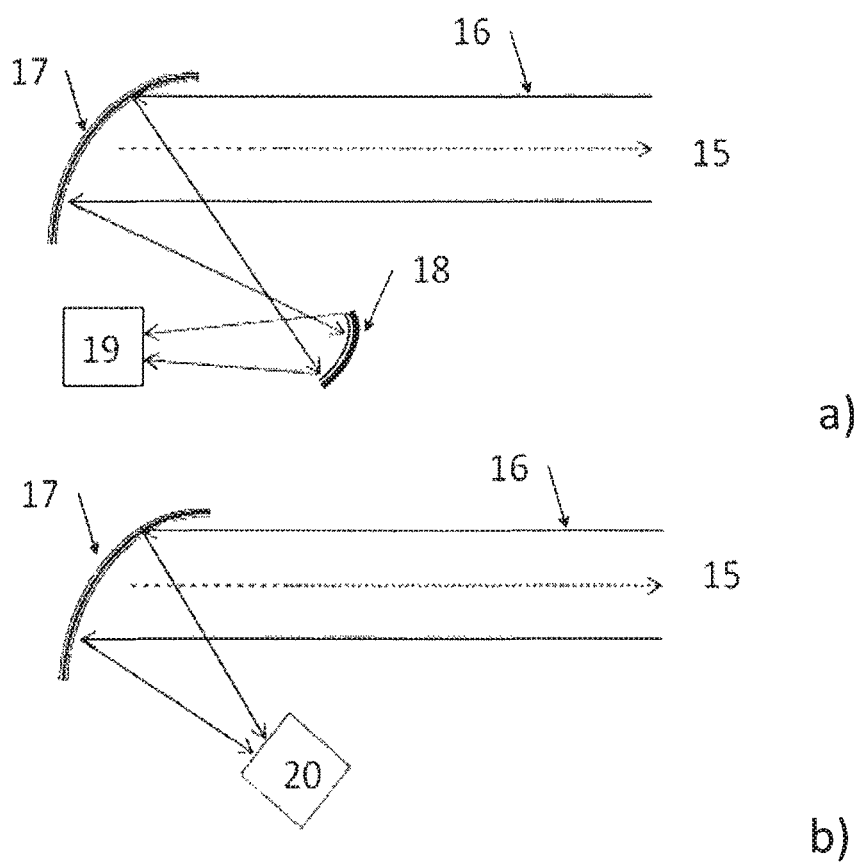
FIG. 3: The scheme of the receiving module; 15—laser beam; 16—return fluorescence flux; 17—off-axis parabolic mirror; 18—concave diffraction grating; 19—multichannel optical detector; 20—detector with discrete spectral channels.

The optimization of operational parameters, weight and size of such device is achieved due to several technical solutions. The receiving module 8 of the LIDAR includes optical telescope and receiving detector with control electronics designed in a single housing. The laser beam 15 is directed along the optical axis of the receiving module 8 based on the off-axis parabolic mirror 17. In one embodiment (FIG. 3a) such mirror 17 is combined with the concave diffraction grating 18 and linear multichannel detector 19 to record and digitize the LIF spectrum. In another embodiment (FIG. 3b) the fluorescence flux 16 is directed by the telescope mirror 17 to the detector 20 constituting the assembly of photo-detectors like an array or a matrix of spectral filters in front of every detector element. The design of the receiving module 8 and the optical schemes according to FIG. 3 minimize the number of optical elements used in the LIDAR receiving module thus providing maximal optical transmission of the LIDAR at minimal dimensions and weight.

Figure 4:
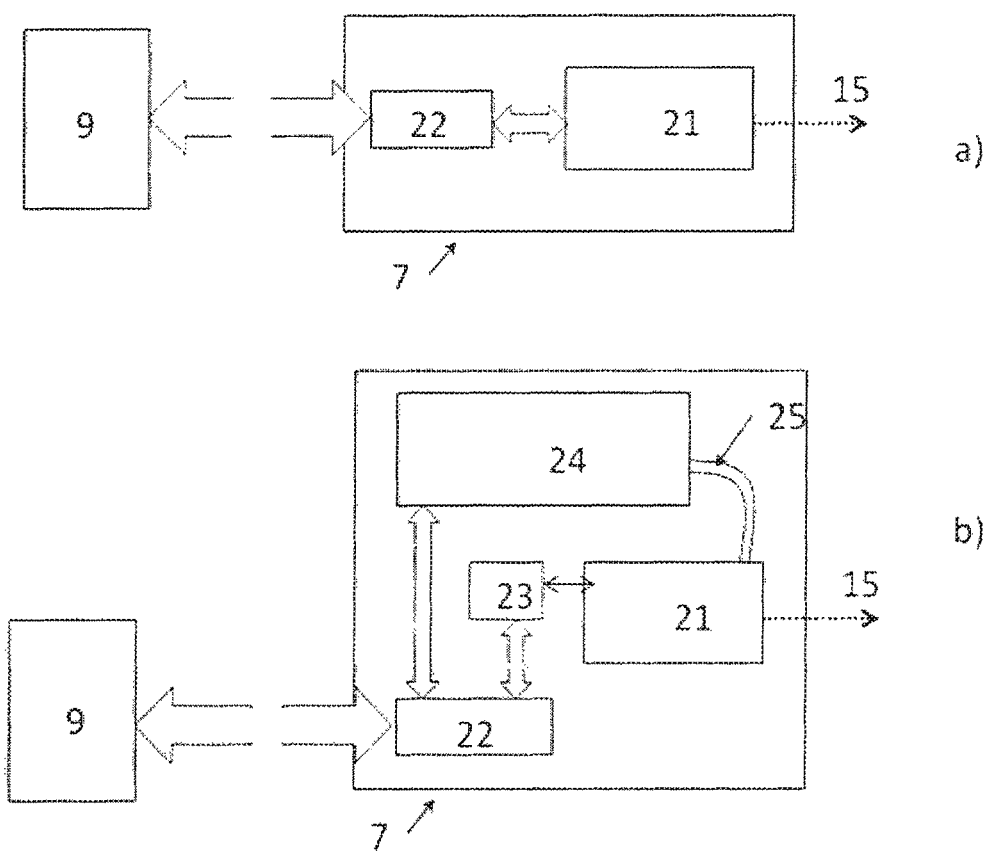
FIG. 4: (a) General scheme of the laser emitter module: 21—pulsed UV-laser; 22—laser controller; (b) The scheme of the laser emitter module based on excimer laser: 23—pulse energy sensor; 24—laser gas filling block; 25—gas pipelines.

FIG. 4 shows the block-scheme of the LIDAR emitter module 8. The LIDAR emitter should operate in pulsed mode in UV spectral range to excite the fluorescence of oil effectively.

When LIDAR is installed on the moving platform, its pulse repetition rate (PRR) and the speed of the platform define the distance between measured spots and therefore— the spatial resolution of pollution map. To provide reasonable fixed spatial resolution, the PRR rate of the laser should be proportional to the platform speed. The laser 21 operation is controlled by laser controller 22 connected with LIDAR controller 9 (FIG. 4a), The LIDAR controller 9 receives GPS coordinates and speed in real-time, calculates the necessary PRR for pre-set spatial resolution and gives the PRR value to the laser controller 22. Then the lasing is provided with variable PRR depending on the speed of movement, and the spatial resolution remains equal to the pre-set value.

The excimer laser (XeCl, 308 nm emission) is known as a highly efficient laser source for its emission wavelength. Such lasers require periodic renewing of the gas mixture. To provide continuous unattended operation of the HLIF LIDAR based on excimer laser, automation of such maintenance is necessary. For this purpose the emitter module 7 is equipped with a pulse energy sensor 23 and an integrated laser gas refilling system 24. The energy of the laser pulse is measured at every laser shot by the sensor 23. When the energy decreases below pre-set threshold due to the laser gas being depleted, the laser controller 22 gives the command to gas refilling system 23, and the laser gas is renewed through the gas pipes 25.

To provide reliable detection of oil on water surface and in water column, the comprehensive LIF spectrum should be correctly recorded and analyzed. First, the recorded LIF spectrum must be recorded with reasonable spectral resolution (hyperspectral) to contain characteristic spectral features of oil and water. In harsh environmental conditions the LIDAR must operate in signal accumulation mode to get fixed Signal-to-Noise (SNR) ratio. It is known that generally the SNR is proportional to the square root of the number N of accumulated spectra: SNR $\sim N^{1/2}$. The measuring cycle is controlled by microcontroller (9) as following. The cycle consists of lasing and recording the induced LIF spectrum, then recording the spectrum of ambient light with following subtraction of the ambient light spectrum from the LIF spectrum. The cycle is repeated until the SNR in accumulated LIF signal reaches the value exceeding the pre-set threshold. When performing the cycle, the LIF spectra recorded from ice pieces are filtered out and not used for accumulation. The possibility of distinguishing water and ice spectra is based on the spectral shape and intensity of ambient light reflected from water containing ice pieces. Indeed, the reflection from ice causes much higher spectral intensities comparing with water reflection (FIG. 5), and LIDAR controller 9 is able to distinguish such spectral shapes.

Figure 5:
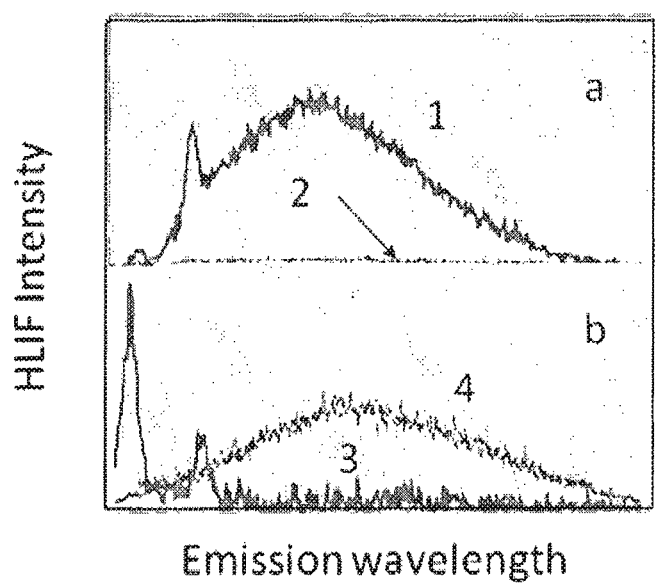
FIG. 5: Examples of HLIF spectra. (a)—clean water 1 and ambient light reflection from clean water 2; (b)—iced water 3 and ambient light reflection from ice 4.

FIG. 5 shows examples of HLIF spectra: (a)—clean water 1 and ambient light reflection from clean water 2; (b)—iced water 3 and ambient light reflection from ice 4.

The module 11 has the storage capacity to save the HLIF raw data combined with GPS and other sensors data, and process the raw data to derive the information about oil pollution and other measured water quality parameters, and transmit the data to the information center through the communication channels. The module 11 should have enough storage capacity to keep the LIDAR data collected over the time interval calculated in a way to prevent data loss in case of limited availability of communication channels.

REFERENCES

1. S. Babichenko. Laser Remote Sensing of the European Marine Environment: LIF technology and Applications. In "Remote Sensing of the European Seas", Vittorio Barale and Martin Gade (Editors), Springer; 2008, 189-204,
2. I. Sobolev, S. Babichenko. Analysis of the performances of hyperspectral lidar for water pollution diagnostics. EARSEL e-Proceedings, Vol. 12, No. 2, 2013, 113-123,
3. S. Babichenko, D. Beynon, and K. O'Neill (2010). Submerged-oil tracking by airborne hyperspectral fluorescent lidar. SPIE Newsroom 10.1117/2.1201011.003273.
4. Boyd Balford Cary, Improved method for removing moisture particles, EP0074441, 1983
5. SINGH AVNIT. Moisture removal apparatus and method, US2008141636, 2008.
6. MOISTURE REMOVAL FILTER, JP2012005991, 2012.
7. BESSANT ALAN. VEHICLE-MOUNTED DEHUMIDIFIER WO2013007982, 2013.

The invention claimed is:

1. A device for remote oil detection comprising the following components:
   (a) an external housing comprising an outlet window (3) through which air can exhaust when the outlet window is open;
   (b) an internal housing, the internal housing being disposed within the external housing, and being hermetically sealed and having an optical window (10);
   (c) a laser module comprising a laser emitter to sense water and induce oil fluorescence;
   (d) a receiving module comprising an optical telescope and spectral detection block to detect a laser induced fluorescence spectrum of an echo-signal;
   (e) a microcontroller module to control device operation and digitize received spectral data; and
   (f) a data processing, storage and communication module for data analysis and reporting,
   wherein the laser module (7), receiving module (8) and microcontroller module (9) are disposed in the hermetically sealed internal housing (6) with optical window (10); wherein the external housing (6) has an ambient air intake (2), mist removal system (4), and heater (5) with temperature sensor to keep the operational temperature of the device at a pre-set level; wherein the components (a)-(e) are disposed with respect to one another such that a laser beam emitted by the laser module and a fluorescence signal received by the receiving module can pass through both the optical window and outlet window and such that, when air is pumped through the ambient air intake at higher than atmosphere pressure, the air circulates through the external housing (1) and exhausts through the outlet window (3) to protect the optical window (10) from salt residuals and frost; and wherein the data processing, storage and communication module (11) is physically separated from the components (a)-(e) of the device and is connected with them for digital data transmission.

2. The device according to claim 1, for remote oil detection wherein the hermetically sealed internal housing (6) with optical window (10) is equipped with a flush module (12) with cleaning liquid, and the optical sensor (14) serves to detect the contamination of the external surface of the optical window (10) by the salt residuals and to start flush to clean the optical window (10); and the internal housing (6) is filled with $N_2$ at overpressure, and wherein the heater (5) with temperature sensor is pre-set to keep the operational temperature of the device at the pre-set level that protects the optical window (10) against the frost.

3. The device according to claim 1, for remote oil detection where the receiving module (8) comprises an off-axis parabolic mirror (17) having an optical axis, and concave diffraction grating (18) coupled with multichannel photodetector (19) to achieve maximal optical transmission of the receiving module for hyperspectral detection of the echo-signal; and the laser module emits a sensing laser beam (15) that is directed along the optical axis of the off-axis parabolic mirror (17) to provide minimal detuning of the device due to variations of sensing distance.

4. The device according to claim 1, where the receiving module (8) comprises an off-axis parabolic mirror (17) and a detector (20) comprising a set of discrete photo-detectors each of which comprises an optical filter, assembled in array or matrix and located out of focus of the off-axis parabolic mirror (17).

5. The device according to claim 1, further comprising a gas refilling system connected to the laser emitter by a pipe and a pulse energy sensor that measures lasing energy of beams emitted by the laser emitter, wherein the laser emitter comprises a compact excimer laser (21) with a laser microcontroller (22), and the laser microcontroller (22) controls operation of the gas refilling system (24) for continuous unattended operation of the laser emitter, and wherein the microcontroller (22) automatically causes the gas refilling system to effect gas refill of the laser emitter when the lasing energy measured with the pulse energy sensor (23) drops below a threshold.

6. The device according to claim 1, wherein the device is disposed on a movable platform and the microcontroller module is configured to receive data from a global positioning system (GPS) as to coordinates and speed of the platform and to calculate a pulse repetition rate (PRR) of the laser emitter required for a desired spatial resolution between measured spots, and for remote oil detection on board of the moving platform, the microcontroller module controls the laser emitter so that the laser emitter emits pulses with the calculated pulse repetition rate to provide a pre-set constant spatial resolution in underway measurements.

7. The device according to claim 1, wherein the device is disposed on a movable platform and the microcontroller module is configured to control the spectral detection block such that the spectral detection block controlled by the microcontroller module (9) accumulates echo-signals until a signal to noise ratio reaches a pre-set value to provide stable quality of recorded spectra in underway measurements.

8. The device according to claim 1, for remote oil detection in iced water, wherein the microcontroller module is configured for recognition of the iced water conditions upon detection of non-zero spectrum of reflection of ambient and excitation light from ice.

9. A device for remote oil detection comprising the following components:
   (a) a laser module comprising a laser emitter to sense water and induce oil fluorescence;
   (b) a receiving module comprising an optical telescope and spectral detection block to detect a laser induced fluorescence spectrum of an echo-signal;
   (c) a microcontroller module to control device operation and digitize received spectral data;
   (d) a data processing, storage and communication module for data analysis and reporting,
   (e) a housing comprising an optical window, the housing being hermetically sealed;
   (f) an optical sensor for detecting contamination from salt residuals on an external surface of the optical window;
   (g) a heater with temperature sensor to keep an operational temperature of the device at a pre-set level that protects the optical window from frost;
   (h) a flush module for supplying cleaning liquid to the optical window; and
   (i) a communication, data processing and storage module for data analysis and reporting;
   wherein the components (a)-(d) and (f)-(h) are disposed inside of the hermetically sealed housing and with respect to one another such that a laser beam emitted by the laser module and a fluorescence signal received by the receiving module can pass through the optical window, and wherein the flush module is configured to release cleaning liquid to remove contamination from the salt residuals from the optical window upon detection of the contamination by the optical sensor.

10. The device according to claim 9, wherein the housing is filled with $N_2$ at overpressure and the heater is pre-set at an operational temperature that protects the optical window against frost.

11. The device according to claim 9, wherein the receiving module comprises an off-axis parabolic mirror having an optical axis, and a concave diffraction grating coupled with multichannel photodetector to achieve maximal optical transmission of the receiving module for hyperspectral detection of the echo-signal; and the laser module emits a sensing laser beam that is directed along the optical axis of the off-axis parabolic mirror to provide minimal detuning of the device due to variations of sensing distance.

12. The device according to claim 9, wherein the receiving module comprises an off-axis parabolic mirror and a detector comprising a set of discrete photo-detectors each of which comprises an optical filter, assembled in array or matrix and located out of focus of the off-axis parabolic mirror.

13. The device according to claim 9, further comprising a gas refilling system connected to the laser emitter by a pipe, and a pulse energy sensor that measures lasing energy of beams emitted by the laser emitter, wherein the laser emitter comprises a compact excimer laser with a laser microcontroller, and the laser microcontroller controls operation of the gas refilling system for continuous unattended operation of the laser emitter, and wherein the laser microcontroller automatically causes the gas refilling system to effect gas refill of the laser emitter automatically when the lasing energy measured with the pulse energy sensor drops below a threshold.

14. The device according to claim 9, wherein the device is disposed on a movable platform and the microcontroller module is configured to receive data from a global positioning system (GPS) as to coordinates and speed of the platform and to calculate a pulse repetition rate (PRR) of the laser emitter required for a desired spatial resolution between measured spots, and wherein the microcontroller module controls the laser emitter so that the laser emitter emits pulses with the pulse repetition rate calculated by the microcontroller module based on GPS data to provide a pre-set constant spatial resolution in underway measurements.

15. The device according to claim 9, wherein the device is disposed on a movable platform and the microcontroller module is configured to control the spectral detection block such that the spectral detection block accumulates echo-signals until a signal to noise ratio reaches a pre-set value to provide stable quality of recorded spectra in underway measurements.

16. The device according to claim 9, wherein for remote oil detection in iced water, the microcontroller module is configured for recognition of iced water conditions upon detection of non-zero spectrum of reflection of ambient and excitation light from ice.

17. The device according to claim 9, further comprising a cleaning liquid supply container disposed outside of the hermetically sealed housing spaced from the optical window, wherein the flush module is disposed inside the hermetically sealed housing spaced from the optical window and is operatively connected to the cleaning liquid supply container to cause cleaning liquid to release from the cleaning liquid supply container upon detection of the contamination by the optical sensor.

* * * * *